(12) United States Patent
Tan et al.

(10) Patent No.: US 7,264,819 B2
(45) Date of Patent: Sep. 4, 2007

(54) **LYASE TREATMENT FOR *P. CARINII***

(75) Inventors: Yuying Tan, San Diego, CA (US);
Zhijian Yang, San Diego, CA (US);
Xinghua Sun, San Diego, CA (US);
Shukuan Li, San Diego, CA (US);
Qinghong Han, San Diego, CA (US);
Mingxu Xu, La Jolla, CA (US)

(73) Assignee: AntiCancer, Inc., San Diego, CA (US)

( * ) Notice: Subject to any disclaimer, the term of this patent is extended or adjusted under 35 U.S.C. 154(b) by 435 days.

(21) Appl. No.: 10/873,583

(22) Filed: Jun. 22, 2004

(65) Prior Publication Data

US 2005/0031606 A1     Feb. 10, 2005

Related U.S. Application Data

(60) Provisional application No. 60/482,047, filed on Jun. 23, 2003.

(51) Int. Cl.
*A61K 39/00*     (2006.01)
*A61K 38/51*     (2006.01)
*A61K 39/385*   (2006.01)
*A61K 38/00*     (2006.01)

(52) U.S. Cl. .............. 424/274.1; 424/94.5; 424/193.1; 514/2

(58) Field of Classification Search ............. 424/274.1, 424/94.5, 193.1; 514/2; 530/350, 825
See application file for complete search history.

(56) References Cited

U.S. PATENT DOCUMENTS

| 5,690,292 | A | 11/1997 | Sano | 242/340 |
| 5,690,929 | A | 11/1997 | Lishko et al. | 424/94.5 |
| 5,715,835 | A | 2/1998 | Lishko et al. | 128/898 |
| 5,888,506 | A | 3/1999 | Tan | 424/94.5 |
| 5,891,704 | A | 4/1999 | Tan | 435/232 |
| 6,231,854 | B1 | 5/2001 | Tan | 424/94.5 |
| 6,461,851 | B1 | 10/2002 | Tan | 435/232 |
| 6,524,571 | B1 | 2/2003 | Xu et al. | 424/93.2 |
| 2002/0035090 | A1 | 3/2002 | Zeldis et al. | 514/43 |

OTHER PUBLICATIONS

Merali et al., J. Biol. Chem. (2000) 275: 14958-14963.
Skelly et al., Lancet (2003) 361: 1267-1268.
Invitation to Pay Additional Fees for PCT/US04/19989, mailed on Sep. 30, 2004, 2 pages.

*Primary Examiner*—S. Devi
(74) *Attorney, Agent, or Firm*—Morrison & Foerster LLP

(57) ABSTRACT

Infection by *P. carinii* can be treated by administering methioninase optionally in combination with additional therapeutic agents, such as antibiotics.

7 Claims, No Drawings

LYASE TREATMENT FOR *P. CARINII*

CROSS-REFERENCE TO RELATED APPLICATION

This application claims benefit under 35 U.S.C. § 119(e) to provisional application U.S. Ser. No. 60/482,047 filed 23 Jun. 2003. The contents of this application are incorporated herein by reference.

TECHNICAL FIELD

The present invention is in the field of treatment for infection, in particular infection by *Pneumocystis carinii*. More specifically, the invention concerns utilization of various lyases to effect such treatment.

BACKGROUND ART

*P. carinii* is the fungus that causes *P. carinii* pneumonia (PCP) in people with depressed immune systems such as AIDS patients, patients undergoing chemotherapy, or transplant patients being treated with immunosuppressants. The currently used drugs that seem most effective are pentamidine and the combination of trimethoprim and sulfamethoxazole. These treatments have severe side effects and the mortality rate remains high. Thus, alternative, more successful treatments for this condition are needed.

A known characteristic of *P. carinii* is that it has an absolute requirement for S-adenosylmethionine (AdoMet) and is unable to synthesize this compound. It apparently scavenges this material from the blood of the infected host. See, Merali, S., et al., *J. Biol. Chem.* (2000) 275:14958-14963. By depleting methionine concentration in the blood, the availability of AdoMet in the blood is also depleted, thus inhibiting the infectious agent.

The uptake of AdoMet by *P. carinii* is verified by the inverse correlation of the level of infection and plasma levels of AdoMet in infected subjects. See, Skelly, M., et al., *Lancet* (2003) 361:1267-1277. Thus, the levels of AdoMet in plasma may be used as a diagnostic method for this infection.

The use of L-methionine-α-deamino-γ-mercaptomethane lyase (methioninase, METase) for the treatment of methionine-dependent tumors, the production of recombinant METase, and modification of METase to reduce antigenicity and enhance half-life by coupling to a polymer such as polyethylene glycol have been described previously in U.S. Pat. Nos. 6,231,854; 6,461,851; 5,888,506; 5,690,292; 5,891,704; and 5,715,835, all incorporated herein by reference. In addition, the use of expression of the gene-encoding methioninase for tumor treatment is described in U.S. Pat. No. 6,524,571, also incorporated herein by reference. According to the present invention, methioninase, optionally in combination with additional antibiotics, is employed in the control of *P. carinii* infection.

DISCLOSURE OF THE INVENTION

The invention takes advantage of the ability of methioninase to deplete the levels of methionine in the blood and thus to deprive the infectious parasite *P. carinii* of its required metabolite, S-adenosylmethionine (AdoMet). Thus, in one aspect, the invention is directed to treat a *P. carinii* infected or potentially infected (exposed) subject which method comprises administering to said subject an amount of methioninase effective to lower the levels of methionine in the blood of said subject and thereby to treat or prevent the *P. carinii* infection. In preferred embodiments, the methioninase is modified to lengthen its biological half-life and reduce antigenicity by coupling the methioninase to a polymer, most conveniently polyethylene glycol.

In another aspect, the invention is directed to pharmaceutical compositions comprising methioninase as an active ingredient in a unit dosage amount effective to treat *P. carinii* infections.

The methioninase may be used in combination with other antibiotics and other drugs known to be effective against this fungus. Even though many of such effective drugs have severe side effects, the use of methioninase in the course of treatment permits sufficient reduction in the supplied amounts of these ancillary drugs to reduce or eliminate these side effects. Thus, in an additional aspect, the invention is related to a method to treat *P. carinii* infected subjects by administering to said subjects, simultaneously or sequentially, amounts of methioninase and at least one additional therapeutic agent effective to treat this condition. In another aspect, the invention is directed to compositions or kits that are combinations of methioninase with an additional drug, preferably an antibiotic.

MODES OF CARRYING OUT THE INVENTION

The basis for the present invention is depletion of methionine in blood and/or cells. Methionine is a precursor of the AdoMet required by *P. carinii*. *P. carinii* has two AdoMet transporters—one of high affinity ($K_m$ of 54.5 mM) and the other of low affinity ($K_m$ of 5,333 mM). The high affinity transporter has a pH optimum of 7.5 and no related natural compounds compete for uptake.

The invention, in all of its aspects, employs a pharmaceutically acceptable form of methioninase. In one embodiment, the methioninase is prepared using recombinant technology as described in the above-cited U.S. patents. In one embodiment, the methioninase is derived from *Pseudomonas putida*; this is a homotetrameric enzyme of 172 kD. METases in general require pyridoxal 5' phosphate (PRP) as a cofactor for activity, and catalyze the hydrolysis of methionine to form α-ketobutyrate, methylmercaptan, and ammonia.

Using the techniques described in the above-cited patents, the recombinantly produced methioninase can be provided in a high degree of purity and substantially free of endotoxins. It is also advantageous, as described, to couple methioninase with a polymer to reduce antigenicity and to enhance half-life in the blood. A particularly convenient formulation is obtained by coupling polyethylene glycol (PEG) to this enzyme.

The methioninase used in the treatment methods of the invention may be administered in appropriate formulations for enzymatically active proteins such as those described in the standard formulary *Remington's Pharmaceutical Sciences*, latest edition, Mack Publishing Co., Easton, Pa., incorporated herein by reference. Typically, the enzyme is administered by injection, including intravenous, subcutaneous, intramuscular, intraperitoneal and the like. Alternatively, the enzyme may be administered using transmucosal or transdermal techniques. Oral administration is also possible, provided appropriate formulation is able to protect the enzyme from degradation in the digestive tract.

The invention also includes kits which contain compositions of methioninase and optionally compositions containing at least one additional therapeutic agent, such as an antibiotic. Typically, if more than one active ingredient is involved, the components are packaged separately as separate compositions. In the kits, the active ingredient compositions are preferably packaged in unit dosage form, for example, already contained in a syringe or other container suitable for effecting administration of the drug.

Generally, the nature of the formulation will depend on the mode of administration. Suitable dosage levels depend on the severity of the infection, the nature of the subject, whether additional antibiotics are included in the treatment, and ultimately on the judgment of the practitioner. Suitable dosage ranges for methioninase administration are in the range of 0.01 mg-500 mg, more usually 0.1 mg-100 mg per typical 70 kg subject per day when administered alone. However, administration at levels outside this range may also be used depending on the factors set forth above. The specific dosage for an individual subject is determined by routine optimization taking account of response as measured by the level of infection and/or the levels of AdoMet circulating in the blood. Suitable subjects for treatment include humans, primates in general, and mammalian and avian subjects.

The success of treatment can be monitored by assessing the levels of AdoMet in blood once the treatment with METase has been cleared. As noted above, the AdoMet plasma concentration is generally inversely correlated with the number of *P. carinii* in the lungs, thus providing a method to assess the success of treatment. (Merali, S., et al., *J. Biol. Chem.* (2000) 275:14958-14963, cited above.) However, during treatment, of course, levels of AdoMet in plasma are diminished.

By "treating" is meant ameliorating the symptoms of the infection, reducing the titer of the infectious organism in the subject, or preventing enhanced levels of titers or preventing enhanced levels of symptomology. Thus, "treatment" includes a general improvement in the condition of the subject as related to the progress (or lack thereof) of the infection.

By "effective amount" is meant an amount which is able to effect successful treatment under the protocol prescribed. Thus, an effective amount of methioninase when administered with an additional therapeutic agent may be less than what is effective if the methioninase is administered alone. Similarly, the effective amount of the additional therapeutic agent may have a smaller lower limit when it is administered with methioninase than would have been the case had it been administered alone.

As noted above, it may be advantageous to provide methioninase in combination with additional therapeutic agents, typically antibiotics. Currently known effective drugs include pentamidine, and the combination of trimethoprim and sulfamethoxazole. These drugs apparently have problematic side effects when used a sole method of treatment; however, in combination with methioninase, the required levels of administration may be reduced to levels which have an acceptable incidence of side effects.

Preparation A:

Preparation of PEGylated Methioninase

Methioninase was prepared recombinantly from the encoding nucleotide sequence isolated from *Pseudomonas putida* and purified as described in U.S. Pat. No. 5,891,704, referenced above. The purified methioninase was coupled with methoxypolyethylene glycol succinimidyl glutarate-500 at various ratios of the PEGylation reagent to recombinant methioninase. Unreacted PEG was removed with Amicon 30K Sentry Prep concentrators or by Sephacryl™ S-300 HR gel filtration chromatography; unreacted METase was removed by DEAE Sepharose® FF anion exchange chromatography. The resulting PEGylated compositions were analyzed by MALDI-TOF mass spectrometry to determine the number of PEG molecules associated with the enzyme. The PEGylated methioninase was injected into mice to determine half-life and depletion time, and antigenicity was determined by titers of IgG and IgM raised by the PEGylated form as compared to recombinant METase lacking PEGylation. The results of these determinations are shown in Table 1.

TABLE 1

| PEGylation agent/ METase ratio | PEG/ METase ratio in product | Fold* increase in Half-Life | Fold* increase in Depletion Time | Fold* decrease IgG PEG-METase | Fold* decrease IgM PEG-METase |
|---|---|---|---|---|---|
| 120/1 | 8-10 | 20× | 10× | $10^{-4}$ | $10^{-3}$ |
| 60/1 | 5-7 | | | $10^{-7}$ | $10^{-3}$ |
| 30/1 | 2-4 | 2× | 4× | $10^{-8}$ | $10^{-4}$ |

*Compared to METase alone.

As shown, the PEGylated product containing 8-10 molecules of PEG per molecule of METase gave a 20-fold increase in half-life, a 10-fold increase in depletion time and showed reduced antigenicity as compared to METase that has not been coupled to PEG. The derivatized product resulting from the 30/1 ratio had an enzyme activity approximately 70% of unmodified METase. PEGylation increases the serum half-life in rats to about 160 minutes compared to 80 minutes for unmodified METase and the PEGylated form depletes serum methionine levels to <0.1 μM for about 8 hours compared to 2 hours for METase itself. The PEG-METase injected intravenously into mice had a tumor/blood retention ratio of about ⅙ compared to 1/10 of unmodified enzyme. See, Tan, Y., et al., *Protein Expression and Purification* (1998) 12:45-52.

After IV administration to nude mice, the distribution of PEG-METase was in the decreasing order blood:kidney:liver:spleen:heart:lung:tumor:intestine:muscle. However, significant levels accumulated in tumor tissue and one hour after injection of 60 units, levels were about 0.026 units/mg protein in human colon tumor growing subcutaneously in nude mice compared to 0.017 units/mg for free METase. See, Tan, et al., supra. In addition, the PEGylation of METase appears to protect against loss of the PRP cofactor. Both METase and PEGylated METase deplete plasma levels of methionine to less than 5 μM in nude mice.

In addition, studies in macaque monkeys using single IV administration of recombinant METase at dosages ranging from 1,000-4,000 U/kg, plasma methionine levels were depleted to an undetectable level by 30 minutes and remained undetectable for four hours. Depletion to less than 1 μM of plasma methionine level at eight hours could be achieved with 4,000 U/kg dosages. However, the un-PEGylated recombinant METase was eliminated rapidly with a halftime of 2.49 hours and some subjects exhibited allergic responses engendered by immune responses to repeated high dosage levels. The benefits of coupling METase to polymer are evident from these results.

Preparation B:

Culture of *P. carinii*

The cells are cultured according to the method of Merali, S., et al., *J. Biol. Chem.* (2000) 275:14958-14963, cited above. *P. carinii* cells are maintained in minimum essential medium with Earle's salts supplemented with 20% horse serum and the following: putrescine, ferric pyrophosphate, L-cysteine, and glutamine. $3 \times 10^6$ cells are placed on 24-mm collagen-coated, 0.4-mm membrane pore size Transwell inserts in 6-well plates. 2.5 ml of medium is added to the wells below the inserts. The Transwell system allows changes of medium without disturbing the cells within the inserts. The medium is changed twice daily and at each change AdoMet stock is added at a final concentration of 500 mM. Cultures are incubated at 31° C. in room temperature.

The following example is offered to illustrate but not to limit the invention.

EXAMPLE 1

A rat model of PCP is prepared according to the methods of Merali, S., et al., *Antimicrob. Agents Chemother.* (1995) 39:1442-1444. Pathogen-free Sprague-Dawley rats are placed in a barrier colony, and given multiple antibiotics to avoid other opportunistic infections. The rats are immunosuppressed by the addition of dexamethasone to the drinking water (1.5 mg liter$^{-1}$).

The rats are then infected with the cultured *P. carinii* of Preparation B.

The rats in the control group are provided only excipient. Rats in test groups are provided various dosages of recombinant METase coupled with polyethylene glycol at various dosages. The rats in the test group show diminished symptoms of *P. carinii* infection.

The invention claimed is:

1. A method to treat *Pneumocystis carinii* (*P. carinii*) infection in a subject in need of such treatment which method comprises administering to said subject an amount of methioninase (METase) effective to lower levels of methionine in the blood of said subject and to treat said infection, wherein said METase is coupled to polyethylene glycol (PEG).

2. The method of claim 1, wherein the methioninase is recombinantly produced.

3. The method of claim 1, wherein the METase is that encoded by the METase-encoding nucleotide sequence of the genome of *Pseudomonas putida*.

4. The method of claim 1, which further includes administering to said subject an effective amount of an additional therapeutic agent.

5. The method of claim 4, wherein said additional therapeutic agent is an antibiotic.

6. The method of claim 5, wherein said antibiotic is pentamidine or is the combination of trimethoprim and sulfamethoxazole.

7. The method of claim 4, wherein said methioninase and said therapeutic agent are administered simultaneously.

* * * * *